United States Patent
Hubler et al.

(10) Patent No.: US 7,129,081 B2
(45) Date of Patent: Oct. 31, 2006

(54) APPARATUS AND METHOD FOR DETECTING MICROORGANISMS

(75) Inventors: Urs Christian Hubler, Basel (CH); Felice Mauro Battiston, Muttenz (CH); Bianca Antje Hermann, Basel (CH)

(73) Assignee: Universitat Basel, Basel (CH)

(*) Notice: Subject to any disclaimer, the term of this patent is extended or adjusted under 35 U.S.C. 154(b) by 549 days.

(21) Appl. No.: 10/375,712

(22) Filed: Feb. 26, 2003

(65) Prior Publication Data

US 2003/0166039 A1 Sep. 4, 2003

(30) Foreign Application Priority Data

Mar. 4, 2002 (DE) ............... 102 09 245

(51) Int. Cl.
*C12M 1/34* (2006.01)
(52) U.S. Cl. ............ 435/287.1; 73/579; 324/750; 324/751; 435/6
(58) Field of Classification Search ............ None
See application file for complete search history.

(56) References Cited

U.S. PATENT DOCUMENTS 5,135,852 A  8/1992  Ebersole

FOREIGN PATENT DOCUMENTS

| DE | 690 03 535 T2 | 2/1991 |
|---|---|---|
| WO | WO 98/50773 A2 | 11/1998 |
| WO | WO 00/58729 A2 | 10/2000 |

OTHER PUBLICATIONS

Prescesky, "Silicon micromachining technology for sub-nanogram discrete mass resonant biosensors," Canadian Journal of Phys., vol. 70, Aug. 7-13, 1992, pp. 1178-1183.
Ilic, "Single cell detection with micromechanical oscillators," J. Vac. Sci. Technol. B., vol. 19, No. 6, Nov. 1, 2001, pp. 2825-2828.
European Search Report for EP 03 40 5136.

*Primary Examiner*—David Redding
(74) *Attorney, Agent, or Firm*—Barnes & Thornburg LLP

(57) ABSTRACT

The present invention relates to the fast detection of microorganisms, i.e. of bacteria, fungi, cells and other organisms, making use of methods and apparatuses coming from nanotechnology. According to the present invention, such organisms are detected using micromechanical sensor means known from many physical and chemical applications. One or more micromechanical cantilever sensors are either coated with a nutritive medium or at least partially built from a nutritive medium. By depositing a microorganism on the cantilever surface, preferably in a targeted way and in a controlled dosage, a "biological reaction" is started. This reaction results in a change of the mechanical and/or electrical properties of the sensor, i.e. the cantilever. These changes are determined, preferably at certain points in time, and thus allow the detection and detailed observation of the applied microorganism.

33 Claims, 4 Drawing Sheets

APPARATUS AND METHOD FOR DETECTING MICROORGANISMS

FIELD OF THE INVENTION

The present invention relates to the fast detection of microorganisms, i.e. bacteria, fungi, cells and other organisms using methods and apparatuses originating from nanotechnology. According to the present invention, these organisms, which are rather difficult and time-consuming to identify with known techniques, are detected using micromechanical sensors. These sensors are well known for their numerous applications in physics and chemistry, e.g. in the fields of surface analysis, chemical sensing or gas analysis by "artificial noses".

DESCRIPTION OF THE PRIOR ART

The applications mentioned above rely mostly on microfabricated cantilevers which are usually fixed to a solid support at one end and able to oscillate freely at the other end. Minimal deflections (bending) of such cantilevers or very small changes in their oscillation behavior are used to determine the quantity in question.

In principle, a change of the mechanical properties and/or behavior of the cantilever is used for detection. The high sensitivity of micromechanical cantilevers becomes manifested in a particular advantage which is difficult to achieve with other methods. Bimetallic cantilever structures are a well-known example of a particular embodiment allowing to detect very small heat quantities, which are e.g. caused by chemical processes at the cantilever surface and result in a minimal asymmetric bending of the cantilever. In another operation mode, small changes in the resonance frequency of a cantilever, caused e.g. by a change in mass, are measured.

So far, cantilever sensors have been functionalized using suitable chemical coatings, e.g. polymers, which are able to bind or adsorb certain molecules more or less selectively. Effects caused by this binding or adsorption process, e.g. surface stress, reaction heat, or a change in mass, result in an easily detectable signal. In principle, binding processes at a chemically functionalized surface are used as a means of detection.

The use of these technologies for biological applications has already been proposed, as is illustrated by the following literature:

Presumably the earliest mentioning of the use of micromechanical cantilevers as biosensors can be found in S. Prescesky et al. in "Silicon micromachining technology for sub-nanogram discrete mass resonant biosensors", Can. J. Phys. Vol. 70 (1992), pp. 1178–1183. The idea to grow living cells on a cantilever surface is found in this publication. The described concept however concentrates on measurements limited to the detection of a mass increase by determining the resonance frequency. Neither cantilever bending caused by surface stress (static mode) nor the use of a nutritive medium to functionalize the cantilever surface is described.

International patent application WO 95/02180 (1993) "Calorimetric Sensor" by Ch. Gerber et al. (IBM) presumably constitutes the earliest intellectual property right on calorimetric sensors based on cantilever arrays.

International patent application WO 98/50773 (1997), D. Charych et al., discloses the detection of biomolecules based on the "key-lock" principle. Thereby specialized receptors are immobilized at the cantilever surface in order to selectively bind, and thereby detect, specific molecules.

A similar description of the detection of molecules using antigen-antibody interactions can be found in international patent application WO 00/58729 (1999) "Micromechanical Antibody Sensors" by T. Thundat et al.

The detection of individual bacteria using antigen-antibody binding is described e.g. by B. llic et al. in "Single cell detection with micromechanical oscillators", J. of Vacuum Science & Technology B, Vol. 19 (2001), pp. 2825–2828.

In other words, today's biological applications of micromechanical cantilever sensors are usually based on highly specific chemical bindings, e.g. antigen-antibody interactions or hybridization of complementary DNA strands. This detection scheme, however, has disadvantages in many respects.

All above implementations and methods need a well-founded knowledge of the organism to be detected as well as a relatively complex preparation of the cantilever surface. Furthermore, these measurements can only be performed in liquids, and no information on the biological activity, e.g. growth rates or effectiveness of drugs like antibiotics, can be obtained.

On the other hand, standard microbiological methods often require a substantial amount of time and a laborious microscopic analysis. More modern methods like immunoassays or DNA tests using PCR are usually complex, time-consuming, and limited to a very specific strain of e.g. bacteria. Depending on the circumstances, these disadvantages can be a serious problem, e.g. in emergency medicine or intensive care.

Another somewhat related method is described by Ebersole et al. in U.S. Pat. No. 5,135,852. Here the activity of microorganisms is detected using a piezoelectric oscillator—not a micromechanical cantilever—and a polymer which reacts with bacterial metabolites by forming complexes. These complexes accumulate on the piezoelectric oscillator, changing its resonance frequency. In order to detect a measurable frequency shift, at least of $10^3$ to $10^5$ microorganisms have to be present. While this method is able to determine the influence of varying conditions on bacterial growth, the bacterial strain still has to grow substantially over time until a signal is detected. All this results in a rather slow reaction and thus renders the method unsuitable for emergency medicine or intensive care.

SUMMARY OF THE INVENTION

The new method according to the invention relies on the high sensitivity of micromechanical sensors, which makes a fast detection possible, but, in contrast to the state-of-the-art methods, does not use binding events at a chemically functionalized surface, but rather directly determines or exploits a biological process occurring at the cantilever surface.

This is achieved by the use of a nutritive medium, which is preferably adapted to the microorganism to be detected, and which is deposited on the cantilever surface. It is therefore not a "chemical" coating of the cantilever, relying on chemical reactions as a means of detection, but a rather a "biological" coating. When a living organism comes in contact with the cantilever surface prepared according to this invention, it will find a favorable environment and hence the possibility to reproduce. This natural reproduction process and the metabolism involved lead to a number of significant changes at the cantilever surface:

As a result of the occurring metabolism and/or the reproduction of the living organism, the applied nutritive coating is modified in its chemical composition and in its geometric structure. This results in a change of the cantilever properties, e.g. an asymmetric change of the surface stiffness, a change in the spring constant, a change of the mechanical oscillation quality factor, (i.e. the resonance frequency divided by the width of the resonance peak at half maximum), a change of the cantilever mass and/or a change in the mass distribution at the cantilever surface. All these quantities, e.g. the bending or the changes in the oscillation behavior, can be detected using established techniques, which are described e.g. by E. Meyer and H. Heinzelmann in R. Wiesendanger and H.-J. Güntherodt (Editors), Scanning Tunneling Microscopy II, Springer Series in Surface Sciences, Vol. 28 (1992).

The metabolism and exchange with the environment, e.g. the use of $O_2$ or of additional nutrients made available from the outside or the release of $CO_2$, lead to a change of the mass and/or the mass distribution at the cantilever surface. These changes in turn lead to a change of the cantilever's resonance frequency, which again can be determined using well-known techniques.

The reproduction process of microorganisms at the cantilever surface leads to substantially different mechanical properties of the cantilever/microorganism system. This results in a deflection of the cantilever, e.g. due to surface stress, or in a change of the cantilever's resonance frequency, e.g. due to a change in mass, in mass distribution or in the cantilever's spring constant. Furthermore, a structural change results in a change of the mechanical oscillation quality factor. Also, all three effects may occur simultaneously. All effects can easily be detected separately or in parallel using well-known techniques.

Further, the heat produced by the microorganisms during metabolism or reproduction yields a deflection of the cantilever. Using a bimorph structure of the cantilever, this deflection can be measured using known techniques.

Generally speaking, the invention includes a micromechanical apparatus and a corresponding method for the detection of the biological activity of microorganisms, in particular their metabolism and/or their reproduction activity, with at least one cantilever and an apparatus designed to measure changes in the mechanical properties of the cantilever. It is characteristic for the invention that a nutritive medium is deposited on the cantilever surface, or that a cantilever is at least partially composed of said nutritive medium. The cantilever can be designed as an easily removable part of a system, i.e. the cantilever can be replaced and, if needed, destroyed after use. This may be a helpful security pre-caution when working with dangerous microorganisms, e.g. harmful bacteria or fungi being the source of highly contagious illnesses.

Besides the characteristic geometry of a cantilever as a plate or spring fixed to a solid support at one end, a number of other geometries could be used for the micromechanical sensor. These range, e.g., from a plate spring-like geometry, fixed to a solid support at both ends to more complex geometries, e.g. a microfabricated torsion spring or a membrane-like structure.

One preferred embodiment comprises an apparatus for applying microorganisms in a targeted way and in a well-defined concentration to the nutritive medium on or of the cantilever.

In another embodiment of the present invention, the cantilever properties, which changed after or by the application of a microorganism, are determined by measuring the deflection and/or the change of the cantilever's oscillation behavior, and a dedicated apparatus is used for this purpose. In this embodiment, the mass change of the cantilever can be measured by observing its resonance frequency shift in a known manner. Further, for determining the structural changes of the cantilever surface, the mechanical damping of its oscillation can be measured.

Changes in cantilever properties may be detected optically, e.g. by using the deflection of a laser beam, or by an electrical signal produced by the cantilever, e.g. when using a piezoelectric cantilever.

Conveniently, the nutritive medium is chosen to match the investigated microorganism, which allows organism-specific measurements.

Another convenient embodiment considers the time factor associated with all biological processes. Thereby cantilever properties are determined only at specific points in time which can be adapted to the investigated microorganism, i.e. the measurement unit is activated only at one or more defined points in time after the application of the microorganism. Another convenient possibility is to record specifically and continuously the time dependence of the cantilever properties and thereby observe exactly the timeline of the biological process.

In a further embodiment, a plurality of cantilevers is arranged in one apparatus, whereby the cantilevers can be coated with or at least partially be composed of different nutritive media and the microorganism to be investigated is applied to more than one cantilever. Conveniently, this multiple arrangement can be designed in such a way as to contain multiple devices for the detection of cantilever properties. Alternatively, at least one detection device is provided which is able to address each cantilever individually. With this embodiment, it is particularly possible to determine a change of cantilever properties at one or more predetermined points in time, especially at those points in time adapted specifically to the investigated microorganism, and thereby to observe or detect the microorganisms.

In another embodiment, the nutritive media deposited on the cantilever or cantilevers can be brought into contact with an active ingredient before or after the application of the microorganisms, e.g. may a specific antibiotic or an active ingredient be added to the nutritive medium. From the detected change in cantilever properties, the effect of such active ingredients on certain microorganisms can be detected fast and reliably. This could constitute a fast test of the effectiveness of certain medication, e.g. when dealing with bacterial strains exhibiting resistance to certain antibiotics.

In an alternative embodiment, the nutritive medium, which is applied to the cantilever surface or which the cantilever is at least partially composed of, does not contain all nutrients essential for the microorganism. The missing nutrients are then made available from the outside, e.g. they are contained within a liquid or gaseous medium surrounding the cantilever. This results in a mass increase during the reproduction process of the microorganisms and/or would allow the study of e.g. the dependence of growth rates from the concentration of certain nutrients. When measuring in liquids, additional precautions can be taken to fix microorganisms and/or the nutritive medium to the cantilever surface.

Yet another embodiment could include means to precisely control the environment of the cantilever/microorganism system. This includes e.g. the measurement and/or control of temperature, relative humidity, or incident light or radiation.

Further embodiments of the apparatus and method according to this invention can be drawn from the following description of various embodiments and from the appended claims.

DESCRIPTION OF THE DRAWINGS

One example of a particular embodiment of the invention will be more closely described on the basis of the following figures.

FIGS. 1a and 1b show an example of a cantilever at two different points in time. Whereas FIG. 1a shows the cantilever immediately after the application of the microorganisms, i.e. at the time t=0, shows FIG. 1b the cantilever after a "biological reaction", i.e. after the microorganisms have multiplied.

FIGS. 2a and 2b show a possible arrangement of several cantilevers building an exchangeable array. FIG. 2a shows an array coated with different nutritive media at the time t=0, i.e. immediately before the injection or deposition (incubation) of microorganisms. After a certain time, the coated cantilevers show different deflections originating e.g. from the composition of the nutritive media, from their treatment with active ingredients and/or from the applied microorganisms. This is shown in FIG. 2b. By this, information e.g. on the type of microorganisms or the effectiveness of a certain active ingredient against (or for) the microorganisms can be obtained. The bent spring is one possibility to fix an exchangeable cantilever array.

In a typical experiment, sterile nutritive agar would be prepared in a manner drawn from a common microbiology text book, or commercially available agar (e.g. from FLUKA) may be used. While the agar is still in its liquid phase, usually above 82° C. (degrees Celsius), it is deposited on the cantilever. This can be done by dipping the cantilever into the liquid agar or by using a spin-coating technique. A typical agar layer on the cantilever surface has a thickness of a few micrometers. Spin-coating allows the fabrication of a well-defined nutritive coating of the cantilever, i.e. the thickness of the layer can be controlled, and the nutritive agar can be applied to only one surface or even only a part of the surface of the cantilever. Extreme care has to be taken that neither the cantilever nor the nutritive agar are contaminated, i.e. this process has to take place under sterile conditions. Sterility could be controlled by observing the coated cantilevers over a certain time period, e.g. by storing them for approximately two days either at ambient conditions or in an incubator. A typical microorganism to be deposited on the coated cantilever and investigated is the bacterium *Escherichia coli* (*E. coli*). This bacterium is rather easily handled, widely used for medical and microbiological research, and, the strain being a natural part of the human intestinal flora, is non-pathogenic. By observing the cantilever deflection as well as its oscillation behavior, the reproduction activity of the *E. coli* bacteria can now be studied under various conditions, e.g. by controlling the temperature, the relative humidity, or the composition of the nutritive agar.

Similar experiments can be conducted using nutritive agar for fungi. This, e.g., allows the study of the growth of yeast.

Figure 3:
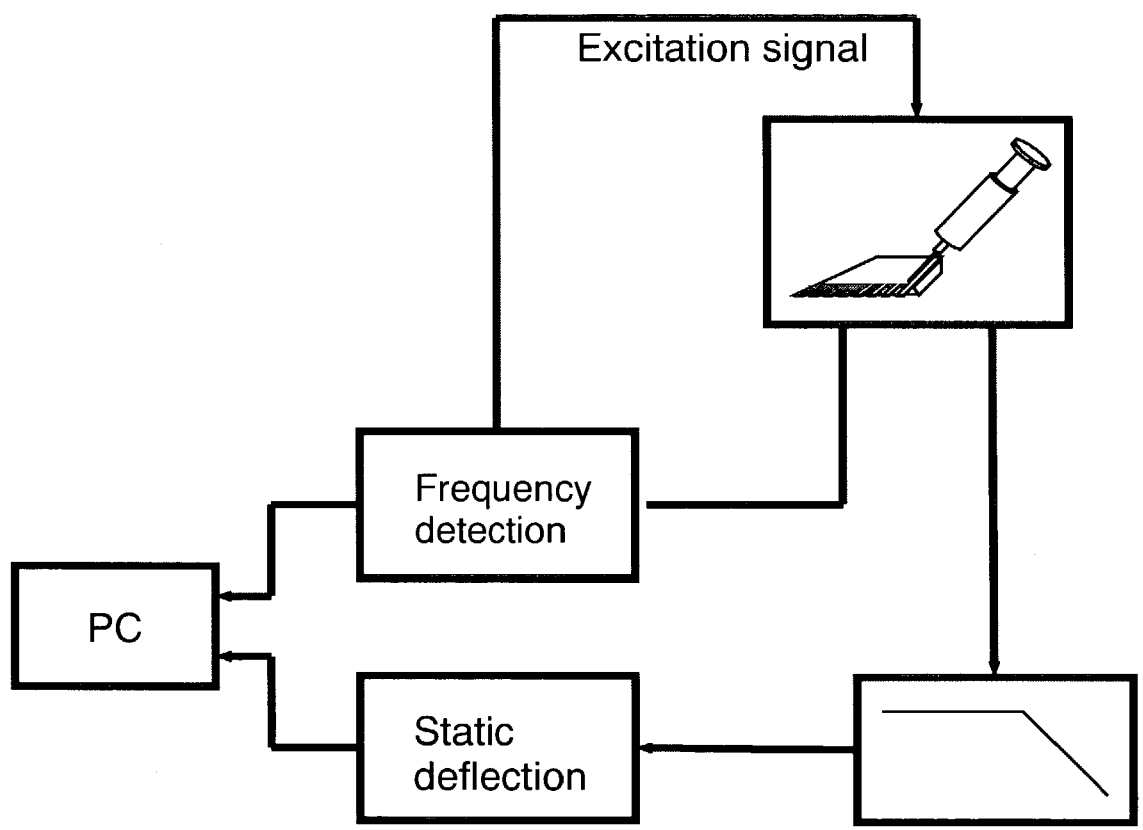
FIG. 3 is a block diagram with different parts of an embodiment according to this invention.

FIG. 3 shows a block diagram with different parts of an embodiment according to the present invention. The cantilever array—shown with an additional symbolic scheme for an apparatus for the deposition of microorganisms—yields electrical signals which correspond to the current deflection of the cantilevers. These signals are directly fed into a frequency-detecting unit, which provides processed data, preferably the current resonance frequencies of the cantilevers, to a computer for visualization and further processing. If needed, electrical signal may be generated in a feedback circuit and used for exciting the cantilever to oscillate.

The DC component, e.g. a low-pass filtered part, of the output signal can be used to detect the static deflection of the cantilever. This DC signal is fed to the PC for visualization and further processing as well.

Figure 4:
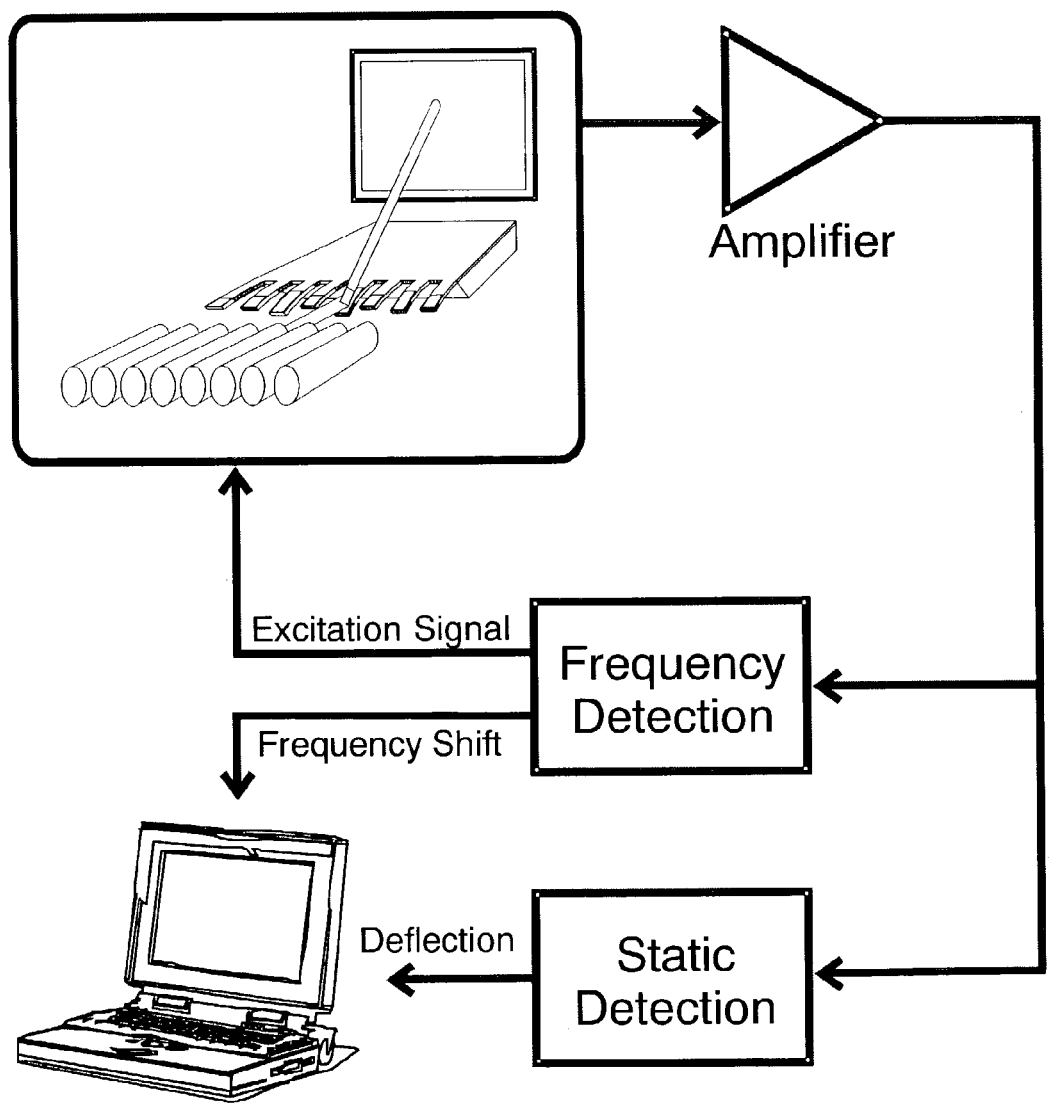
FIG. 4 shows another arrangement with several cantilevers.

FIG. 4 shows an embodiment of the current invention using several cantilevers. An arrangement of eight cantilevers illuminated one after the other with eight light sources provides the quasi-parallel detection of cantilever deflection and resonance frequency. The deflection of the light beam is measured using a position-sensitive photodetector (PSD), whose output signal is electronically amplified and fed to an electronic circuit to determine the resonance frequency and the static deflection, e.g. the equilibrium point of the oscillation. The resulting data are visualized, analyzed and processed with the help of a computer. Beside the beam deflection method shown in this figure, other optical or electronic detection methods are conceivable: interferometric or piezoelectric detection schemes are two well-known examples for alternative detection methods.

Figure 2B:
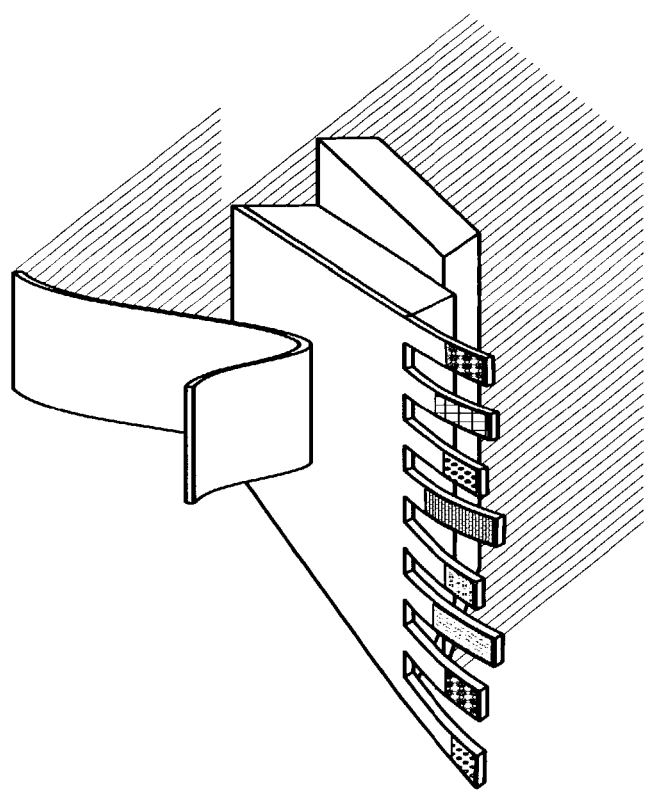
FIGS. 2a and 2b depict an arrangement of several cantilevers.
Figure 2A:
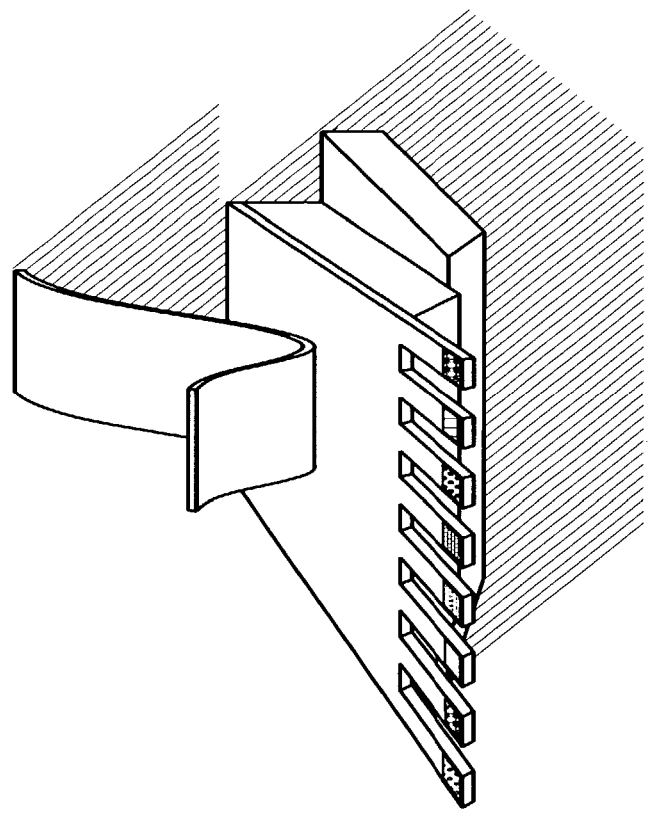

In an experiment using an array of micromechanical cantilevers, each cantilever would typically be coated with a different nutritive agar. While one cantilever is coated with "common" nutritive agar as described above in relation to FIGS. 2a and 2b, the other cantilevers is coated with agar containing various antibiotics against bacteria, e.g. ampicillin, kanamycin, or zeocin, all of which are commercially available. When the whole cantilever array, i.e. each cantilever, is brought into contact with an *E. coli* strain exhibiting no antibiotics resistance, bacterial growth occurs on the lever with the "common" agar only. This results in a significant deflection of this particular cantilever, while all other cantilevers exhibit no change in their deflection. If, however, an *E. coli* strain exhibiting resistance to the antibiotic ampicillin is applied to the cantilever array, growth occurs on the "common" agar as well as on the agar containing ampicillin. The signature of the cantilevers showing a substantial deflection is then characteristic of an ampicillin-resistant *E. coli* strain.

As understood by a person skilled in the art, resistant *E. coli* strains can easily be grown using standard genetic techniques.

Instead of the cantilever deflection, the oscillatory properties of each cantilever can be observed. During bacterial growth, changes in the mass distribution and/or the surface structure of the cantilever occur. This is caused by the two-dimensional inhomogeneous replication process of the bacteria and results in a resonance frequency shift and/or a change in the quality factor, which can be used as an indication of bacterial growth.

In a clinical environment, this method could be used with pathogenic bacteria strains to get quick results on potential antibiotics resistance and can thus avoid ineffective treatment with the wrong antibiotic.

In a similar experiment, individual cantilevers are coated with differently composed nutritive agars, many of which are commercially available (e.g. from Merck or Fluka). A certain strain of *E. coli*, for example, grows well on a plate count agar (i.e. nutritive medium containing tryptone, yeast extract, dextrose, agar) coated cantilever, while salmonellae grow better on e.g. *Rambach agar* (i.e. nutritive medium containing peptone, sodium chloride, sodium deoxycholate, propylene glycol, agar-agar). The characteristic fingerprint of different cantilever deflections and/or different resonance frequency shifts are now used to identify the type of microorganism that is present and an at least partial selectivity can be obtained. This recognition process can be automated, using an artificial neural network trained to attribute a certain "cantilever fingerprint" to a bacteria strain.

When using a cantilever array, it may be preferable to measure the variation or change of deflection between individual cantilevers as opposed to the absolute deflection of a single cantilever. This would eliminate any effect of changes in the deflection of the whole array, e.g. caused by temperature fluctuations or other external distortions.

Figure 1:
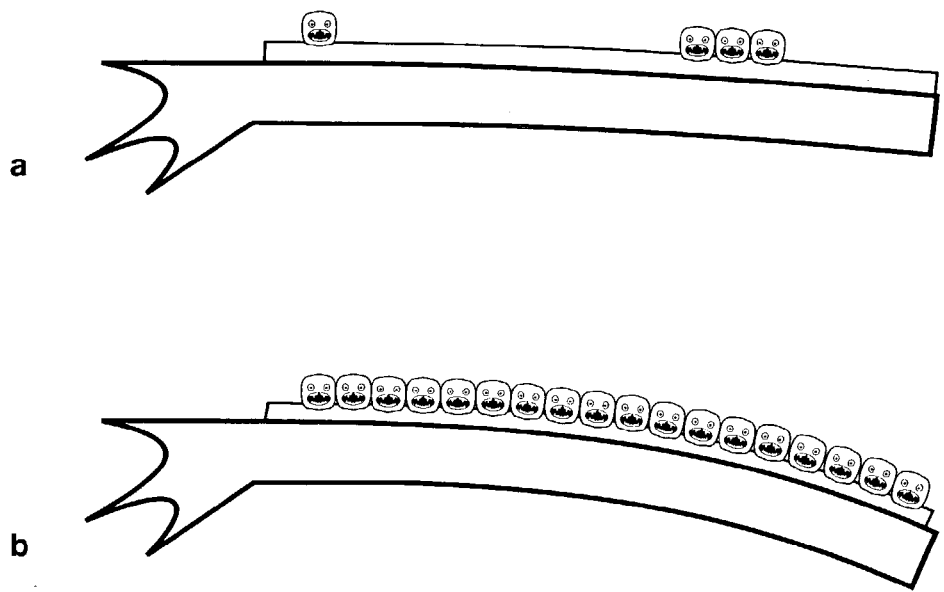
FIGS. 1a and 1b show a cantilever according to this invention.
Figure 5:
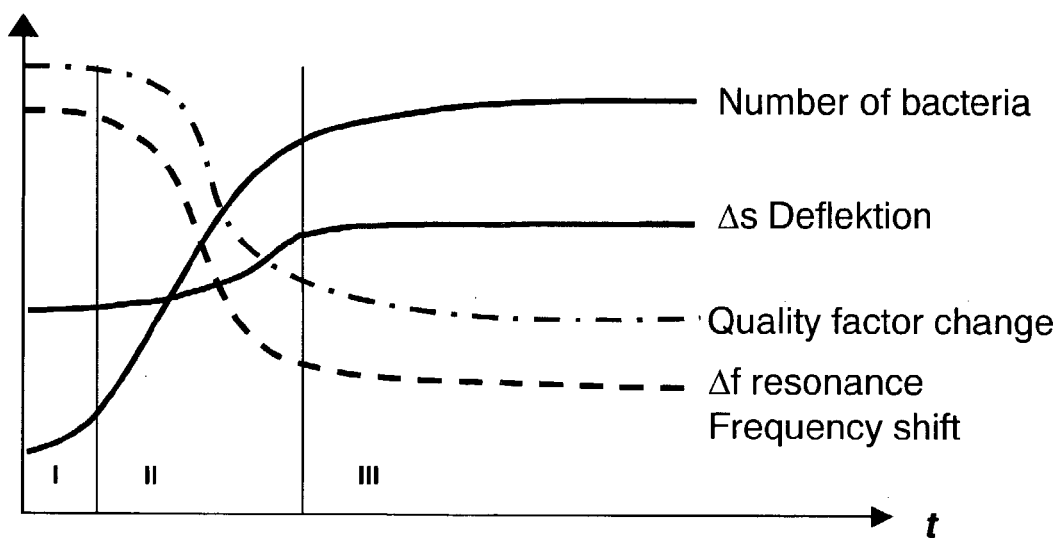
FIG. 5 are schematic measurement curves resulting from the reproduction of bacteria on the cantilever.

FIG. 5 finally shows a schematic measurement result which reflects the timeline of the signal resulting from the reproduction of bacteria on the cantilever surface, i.e. the resonance frequency shift $\Delta f$, the change in the quality factor $\Delta Q$ (damping change) and/or the static change in deflection $\Delta s$. The quality factor is defined as the ratio between the resonance frequency and the width of the resonance peak at half maximum. After an initial lag phase (I), during which the microorganism adapts to the new environment and during which only slow growth and only minimal impact on the measured signal occurs, the log phase (II) follows. This phase is characterized by exponential growth of the microorganism population. The decrease in mass, e.g. by the release of $CO_2$ during the production of ATP (Adenosine Tri-Phosphate), leads to a increase of the resonance frequency f of the cantilever, while at the same time its static deflection (equilibrium point) increases too. On the other hand, if a nutritive medium is supplied from outside, the total mass of the cantilever increases, resulting in a decrease of the resonance frequency, as shown in FIG. 5. Furthermore, due to the local growth of microorganisms, the surface becomes inhomogeneous in its structure, and therefore the quality factor Q drops. Once saturation is reached in the stationary phase (III), no change in the measurement signals occurs anymore.

The implementation of the functionalities described above provides no difficulty for a person skilled in the art. Also, all of the methods, steps and apparatus disclosed and claimed herein can be made and executed without undue experimentation. Further, materials and compositions given herein may be substituted by related chemically and/or biologically related materials and compositions while the same or similar results are achieved.

Also, software is commercially available for many partial functions. Where this is not the case, such software can easily be written by someone skilled in the art.

The invention claimed is:

1. A micromechanical apparatus for the detection of a biological activity of a microorganism, the apparatus comprising at least one micromechanical cantilever and means for identifying a change in a property of said cantilever, including said cantilever comprising a nutritive medium at least partly extending on its surface, handling means for bringing said microorganism in contact with said nutritive medium, said identifying means being designed to determine the deflection and/or the oscillation behavior of the cantilever resulting from or as a consequence of the added microorganism, said oscillation behavior being determined by at least one of the following quantities:

(a) the shift in resonance frequency;

(b) the mechanical damping of the resonance amplitude;

(c) the phase shift between the cantilever excitation and oscillation, thus determining a change in a property of said cantilever and relating it to said biological activity of said microorganism.

2. The micromechanical apparatus according to claim 1, wherein the identifying means comprises a light source and a detector for measuring the position of a light beam reflected by the cantilever surface.

3. The micromechanical apparatus according to claim 1, wherein the identifying means comprises interferometric means for determining a cantilever property.

4. The micromechanical apparatus according to claim 1, wherein the identifying means comprises means for determining an electrical property, of the cantilever or of the nutritive medium.

5. The micromechanical apparatus according to claim 1, wherein the handling means comprises dosage means for applying the microorganism targeted and/or in a predefined dosage to the nutritive medium.

6. The micromechanical apparatus according to claim 1, wherein the nutritive medium is chosen to be adapted to the investigated microorganism and/or contains active ingredients, for or against said microorganism.

7. The micromechanical apparatus according to claim 1, wherein the nutritive medium on or in the cantilever lacks an essential nutrient and said missing essential nutrient is made available from the outside.

8. The micromechanical apparatus according to claim 1, further including timing means adapted to activate the identifying means at one or more predetermined times.

9. The micromechanical apparatus according to claim 8, wherein the timing means is adapted to be activated continuously, allowing a continuous determination of a cantilever property.

10. The micromechanical apparatus according to claim 1 with a plurality of cantilevers, whereby at least one of said cantilevers is coated with or at least partially composed of a nutritive medium and/or an active ingredient, which nutritive medium and/or active ingredient is different from the nutritive media and/or active ingredients of at least one of the remaining cantilevers.

11. The micromechanical apparatus according to claim 10, wherein the handling means is adapted to apply the investigated microorganism to more than one of the plurality of cantilevers.

12. The micromechanical apparatus according to claim 10, further including a plurality of identifying means.

13. The micromechanical apparatus according to claim 10, including identifying means adapted to be activated separately for each cantilever.

14. A method for detecting the activity of a microorganism using a micromechanical apparatus according to claim 1 including (a) applying said microorganism to a nutritive medium present on or in said cantilever, or which said cantilever is at least partially composed of;
(b) having said microorganism interact with said nutritive medium;
(c) determining at least one changed property of said cantilever.

15. The method according to claim 14, wherein the microorganism is applied in a targeted way and a defined dosage to the nutritive medium.

16. The method according to claim 14, wherein the change of a property of the cantilever as a consequence of the applied microorganism is determined from the deflection and/or change in the oscillation behavior of said cantilever.

17. The method according to claim 16, wherein the change of the oscillation behavior of the cantilever is determined by measuring at least one of the following quantities:
(a) the resonance frequency shift;
(b) the mechanical damping of the resonance amplitude;
(c) the phase shift between the cantilever excitation and oscillation.

18. The method according to claim 14, wherein the change of a property of the cantilever is determined from the movement of a light beam reflected by the cantilever surface.

19. The method according to claim 14, wherein the change of a property of the cantilever is determined from the interference between a reference light beam and a light beam reflected by the cantilever surface.

20. The method according to claim 14, wherein the change of a property of the cantilever is determined from a change of an electrical property of said cantilever or said nutritive medium on said cantilever.

21. The method according to claim 14, wherein the nutritive medium is adapted to said microorganism.

22. The method according to claim 14, wherein the nutritive medium on or in the cantilever lacks an essential nutrient and said missing essential nutrient is made available from the outside.

23. The method according to claim 14, wherein, the changed properties of the cantilever are determined at one or more points in time, specifically points in time adapted to said microorganism.

24. The method according to claim 14, wherein the change of a property of the cantilever is monitored continuously.

25. The method according to claim 14 using a micromechanical setup with a plurality of cantilevers, wherein
(a) said cantilevers are coated or at least partially composed of different nutritive media and
(b) the microorganism is applied to more than one cantilever.

26. The method according to claim 25, wherein the properties of the cantilevers are monitored continuously.

27. The method according to claim 25, wherein the property of a cantilever is determined for each cantilever individually.

28. The method according to claim 25, wherein a changed property of a cantilever is determined for each cantilever at a different point in time after application of said microorganism.

29. The micromechanical apparatus according to claim 1, wherein the biological activity of the microorganism is its metabolism and/or its reproduction activity.

30. The micromechanical apparatus according to claim 1, wherein the cantilever consists of a nutritive medium.

31. The micromechanical apparatus according to claim 1, wherein the identifying means comprises means for determining a change in resistance or in dielectrical constant of the cantilever or of the nutritive medium.

32. The micromechanical apparatus according to claim 6, wherein the nutritive medium contains medication for or against said microorganism as an active ingredient.

33. The micromechanical apparatus according to claim 8, wherein the timing means is adapted to the investigated microorganism.

* * * * *

UNITED STATES PATENT AND TRADEMARK OFFICE
CERTIFICATE OF CORRECTION

PATENT NO. : 7,129,081 B2  
APPLICATION NO. : 10/375712  
DATED : October 31, 2006  
INVENTOR(S) : Urs Christian Hubler et al.

Page 1 of 1

It is certified that error appears in the above-identified patent and that said Letters Patent is hereby corrected as shown below:

On the Title Page, insert at (73) Assignee to read

-- Concentris GmbH, Basel (CH)

and

Universität Basel, Basel (CH) --

Signed and Sealed this

Nineteenth Day of August, 2008

JON W. DUDAS  
*Director of the United States Patent and Trademark Office*